United States Patent
Venkataramani et al.

(10) Patent No.: US 6,706,212 B2
(45) Date of Patent: Mar. 16, 2004

(54) CERIUM-DOPED ALKALINE-EARTH HAFNIUM OXIDE SCINTILLATORS HAVING IMPROVED TRANSPARENCY AND METHOD OF MAKING THE SAME

(75) Inventors: Venkat Subramaniam Venkataramani, Clifton Park, NY (US); Sergio Martins Loureiro, Albany, NY (US); Manisha Vishwanath Rane, Schenectady, NY (US)

(73) Assignee: General Electric Company, Niskayuna, NY (US)

( * ) Notice: Subject to any disclaimer, the term of this patent is extended or adjusted under 35 U.S.C. 154(b) by 27 days.

(21) Appl. No.: 10/121,363

(22) Filed: Apr. 12, 2002

(65) Prior Publication Data

US 2003/0193040 A1 Oct. 16, 2003

(51) Int. Cl.$^7$ ............................ C09K 11/55; C09K 11/67
(52) U.S. Cl. ........................... 252/301.4 F; 250/363.4; 250/363.03
(58) Field of Search .............. 252/301.4 R; 250/363.04, 250/363.03

(56) References Cited

U.S. PATENT DOCUMENTS

| | | | |
|---|---|---|---|
| 5,015,860 A | 5/1991 | Moses | 250/361 R |
| 5,039,858 A | 8/1991 | Anderson et al. | 250/363.03 |
| 5,124,072 A | * 6/1992 | Dole et al. | 252/301.4 F |
| 5,134,293 A | 7/1992 | Anderson et al. | 250/363.03 |
| 5,786,600 A | * 7/1998 | Lambert et al. | 250/484.4 |

OTHER PUBLICATIONS

Venkat S. Venkataramani et al., "Ceramic Routes to Transparent Scintillators," IEEE 2001 Nuclear Science Symposium and Medical Imaging Conference, Nov. 4–10, 2001, San Diego, California.

* cited by examiner

*Primary Examiner*—C. Melissa Koslow
(74) *Attorney, Agent, or Firm*—Toan P. Vo; Patrick K. Patnode (57) ABSTRACT

Cerium-doped alkaline-earth hafnium oxide scintillator compositions have at least one alkaline earth metal selected from the group consisting of Ba, Sr, Ca, and combinations thereof. The scintillator compositions can be formed into a shape having porosity less than about 0.05 percent for improved transparency. The alkaline earth metal can be partially substituted with divalent and/or trivalent ions other than cerium. Hafnium can be partially substituted with divalent, trivalent, and/or tetravalent ions. The scintillators are characterized by high light output, short decay time, and high radiation stopping power. The scintillators can be used as detector elements in PET systems.

62 Claims, 4 Drawing Sheets

CERIUM-DOPED ALKALINE-EARTH HAFNIUM OXIDE SCINTILLATORS HAVING IMPROVED TRANSPARENCY AND METHOD OF MAKING THE SAME

BACKGROUND OF THE INVENTION

The present invention relates to cerium-doped alkaline earth scintillators useful for the detection of high-energy radiation. In particular, the present invention relates to a shaped cerium-doped alkaline-earth hafnium oxide scintillator having improved transparency and light output for use in positron emission tomography. The present invention also relates to detectors and detection systems incorporating a scintillator comprising polycrystalline cerium-doped alkaline earth hafnium oxide.

Positron emission tomography ("PET") is a medical imaging technique in which a radioactively labeled substance is administered to a patient and then traced within the patient's body by means of an instrument that detects the decay of the radioactive isotope. In PET, a chemical tracer compound having a desired biological activity or affinity for a particular organ is labeled with a radioactive isotope that decays by emitting a positron. The emitted positron loses most of its kinetic energy after traveling only a few millimeters in a living tissue. It is then highly susceptible to interaction with an electron, an event that annihilates both particles. The mass of the two particles is converted into 1.02 million electron volts (1.02 MeV) of energy, divided equally between two 511 keV photons (gamma rays). The two photons are emitted simultaneously and travel in almost exactly opposite directions. The two photons penetrate the surrounding tissue, exit the patient's body, and are absorbed and recorded by photodetectors typically arranged in a circular array. Biological activity within an organ under investigation can be assessed by tracing the source of the radiation emitted from the patient's body to the photodetectors.

The value of PET as a clinical imaging technique is in large measure dependent upon the performance of the photodetectors. Each photodetector comprises a scintillator cell or pixel coupled to photomultiplier tubes. When a photon generated from an annihilation of the positron strikes a scintillator cell, it excites the scintillator material to produce light that is sensed by the photomultiplier tubes. The electrical signals from the photomultiplier tubes are processed to produce an image of the patient's organ. The scintillator material desirably has good stopping power, high light output, and fast decay time. Stopping power is the ability to stop the 511 keV photons in as little materials as possible so as to reduce the overall size of the photodetectors and, therefore, enhance the light collection efficiency and energy resolution. Stopping power is typically expressed as the linear attenuation coefficient $\tau$ having units of inverse centimeters ($cm^{-1}$). After a photon beam has traveled a distance x in a scintillator material, the proportion of photons that has not been stopped by the scintillator material is $\exp(-\tau \cdot x)$. Thus, for a good scintillator material, $\tau$ should be as large as possible. High light output is important because the photodetectors will have higher sensitivity, and, thus, the dose of the radioactive material administered to the patient can be reduced. Decay time (or also known as time constant, decay constant, or primary speed) is a measure of how fast the scintillator material stops emitting light after a cessation of excitation by the 511 keV photon. Short decay time allows for more rapid scanning, and, thus, better observation of the motion of the body's organs. Known scintillator materials for PET are thallium-doped sodium iodide (NaI:Tl), cesium fluoride (CsF), barium fluoride ($BaF_2$), and bismuth germanate ($Bi_4Ge_3O_{12}$ or "BGO"). Each of these scintillator materials has something left to be desired. NaI:Tl has a good stopping power but a long decay constant of about 250 nsec (nanoseconds). CsF has relatively poor stopping power of about 0.43 $cm^{-1}$ and is highly hygroscopic. BGO has a relatively good stopping power but a relatively low light output and a long decay constant of about 300 nsec. Although $BaF_2$ is not as hygroscopic as CsF, it has a poor stopping power similar to that of CsF and a much longer decay constant of about 620 nsec.

Therefore, there is a continued need for scintillator materials for PET that have better properties than those currently available.

SUMMARY OF THE INVENTION

The present invention provides improved scintillator compositions comprising alkaline earth hafnium oxide doped with cerium. The scintillator compositions are useful in the detection of high-energy radiation, such as X, $\beta$, or $\gamma$ radiation. Particularly, the scintillators of the present invention have improved light output, short decay time, and high stopping power in positron emission tomography applications. The scintillator compositions of the present invention has a general formula of $AHfO_3$:Ce; wherein A is an alkaline earth metal selected from the group consisting of barium, strontium, calcium, and combinations thereof; and the atomic ratio of A:Hf is from about 0.9:1 to about 1.1:1. In this formula, Ce written after the colon represents the dopant. Ce is present in an amount from about 0.005 atom percent to about 5 atom percent.

In one aspect of the present invention, the alkaline earth metal is partially substituted with at least one trivalent ion or one divalent ion.

In another aspect of the present invention, hafnium is partially substituted with at least one divalent ion, one trivalent ion other than cerium, one other tetravalent ion, or combinations thereof.

According to one aspect of the present invention, a method for producing a scintillator material comprising a polycrystalline alkaline earth hafnium oxide doped with cerium, the scintillator being useful for a detection of X, $\beta$, or $\gamma$ radiation, comprises the steps of: (1) providing amounts of compounds of at least cerium, hafnium, and at least an alkaline earth metal selected from the group consisting of barium, strontium, calcium, and combinations thereof; the amounts of the compounds being selected such that the final composition of the scintillator material is achieved; (2) mixing together the compounds to form a mixture; and (3) firing the mixture at a temperature and for a time sufficient to convert the mixture to an alkaline earth hafnium oxide doped with cerium.

According to another aspect of the present invention, the method further comprises conducting a hot isostatic pressing of powder of the alkaline earth hafnium oxide doped with cerium to form a shaped polycrystalline scintillator that has improved light transparency.

In still another aspect of the present invention, a detector is provided for PET and comprises a polycrystalline scintillator comprising an alkaline earth hafnium oxide doped with cerium having a general formula of $AHfO_3$:Ce; wherein A is at least an alkaline earth metal selected from the group consisting of Ba, Sr, Ca, and combinations thereof; the atomic ratio of A:Hf is from about 0.9:1 to about 1.1:1; and Ce is present in an amount from about 0.005 atom percent to about 5 atom percent.

In still another aspect of the present invention, such a detector is incorporated in a PET system.

Other features and advantages of the present invention will be apparent from a perusal of the following detailed description of the invention and the accompanying drawings in which the same numerals refer to like elements.

DETAILED DESCRIPTION OF THE INVENTION

Figure 1:
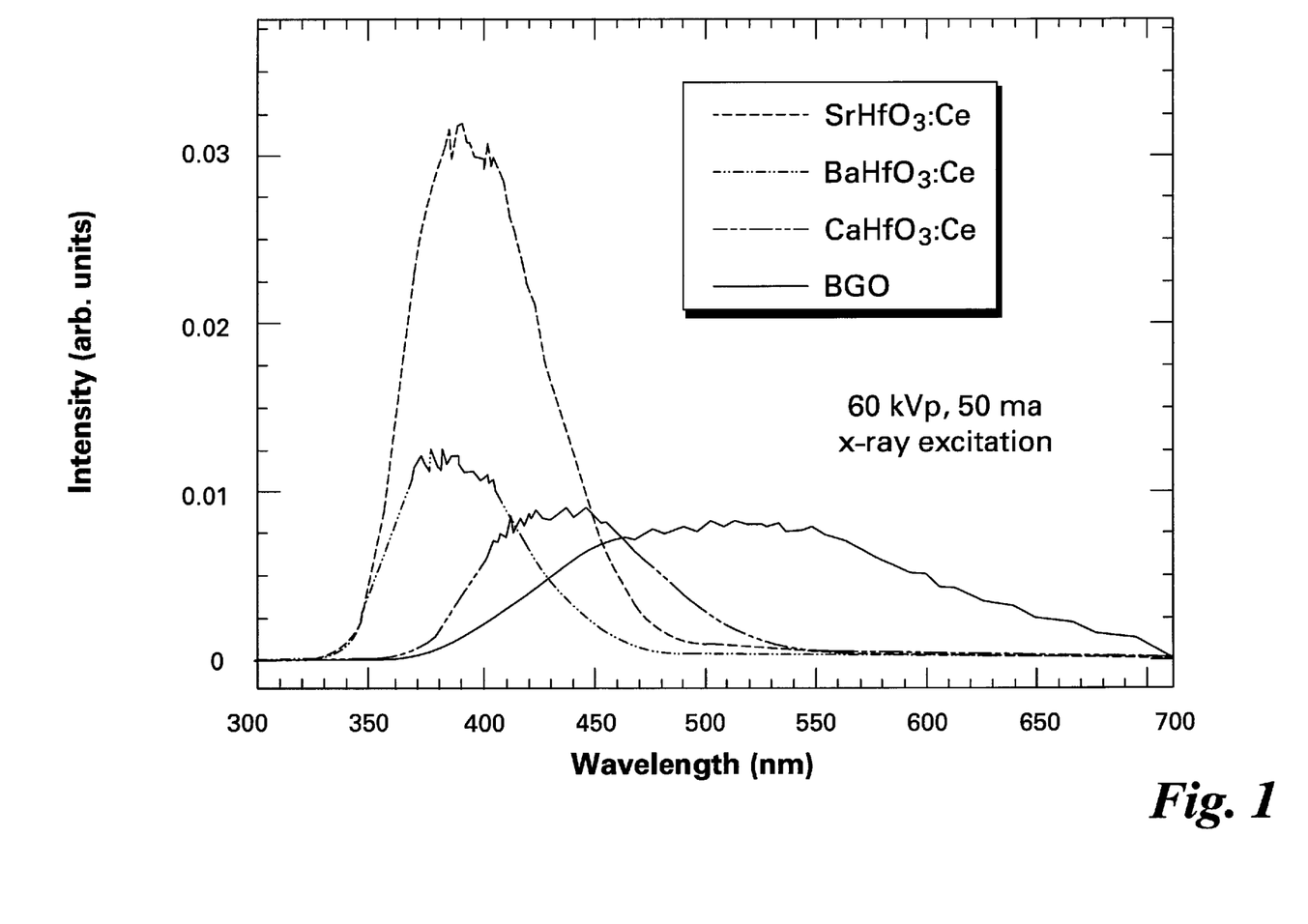
FIG. 1 shows emission spectra of $SrHfO_3$:Ce, $BaHfO_3$:Ce, and $CaHfO_3$:Ce compared to an emission spectrum of BGO.
Figure 2:
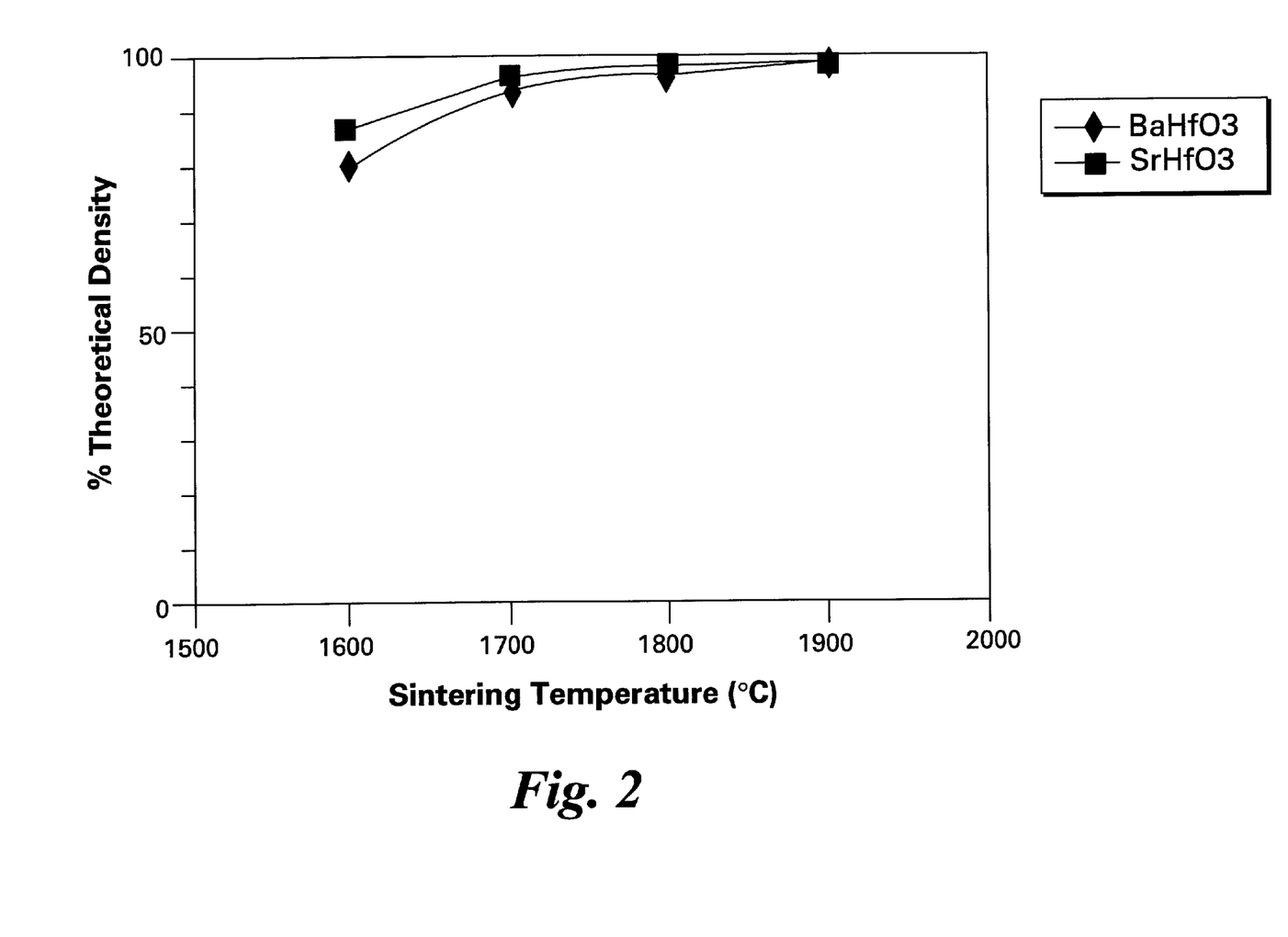
FIG. 2 shows the effect of sintering temperature on the density of $SrHfO_3$:Ce and $BaHfO_3$:Ce.
Figure 3:
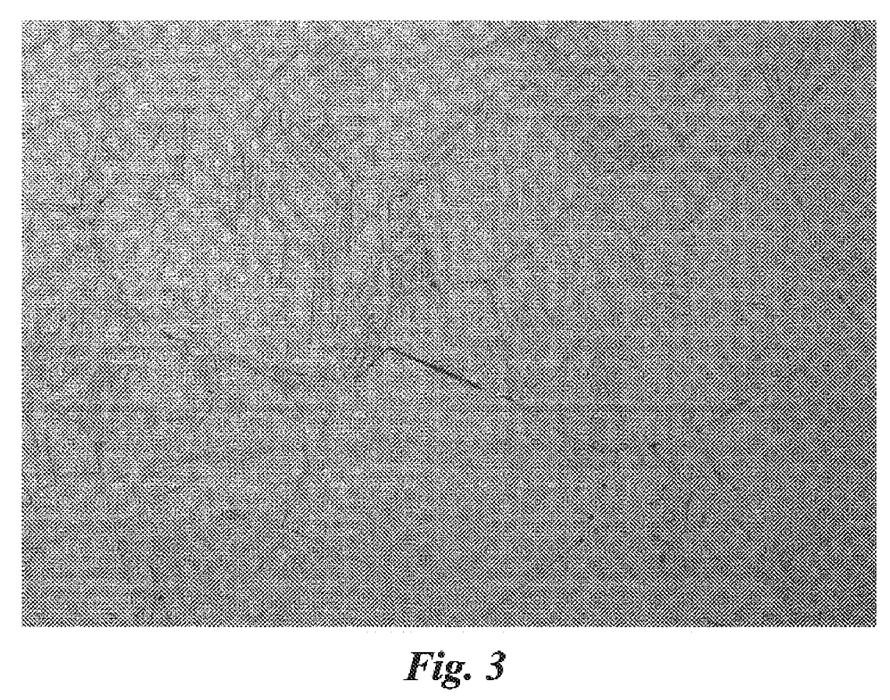
FIG. 3 is an electron micrograph of $SrHfO_3$:Ce after undergoing sintering and hot isostatic pressing.
Figure 4:
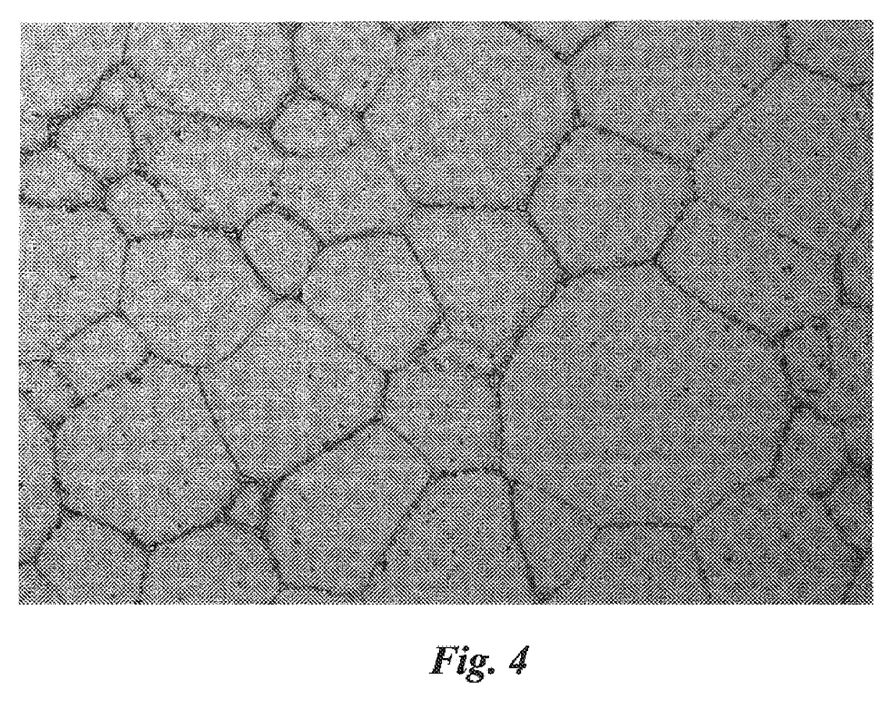
FIG. 4 is an electron micrograph of $SrHfO_3$:Ce after undergoing sintering, hot isostatic pressing, and annealing.

The present invention provides polycrystalline cerium-doped alkaline earth hafnium oxide scintillator that comprises at least an alkaline earth metal selected from the group consisting of barium, strontium, calcium, and combinations thereof. All metals disclosed herein are present in the scintillator compositions in association with oxygen, rather than in elemental form. In one aspect of the present invention, the scintillators are responsive to gamma-ray excitation and have improved light output, short decay time, and high gamma-ray stopping power.

As used herein, the term "light output" is the quantity of visible light emitted by the scintillator after being excited by a pulse of radiation having an average intensity of about 60 keV and a duration of 500 milliseconds. For ease of comparison, the light output presented in this disclosure is a relative quantity compared to the light output of a BGO scintillator standard. The term "decay time," "primary decay," or "primary speed" is the time required for the intensity of the light emitted decreases to about 36.8% (or 1/e) of the light intensity at the time after the excitation with 60 keV radiation ceases. The term "stopping power" refers to the ability of a material to absorb radiation, also commonly called the attenuation or absorption coefficient, reported in $cm^{-1}$. A material having a high stopping power allows little or no gamma radiation to pass through. The stopping power is directly related to the density of the scintillator and the elements contained therein. Thus, it is advantageous to produce scintillators having high density, preferably near a theoretical density. Higher light output is advantageous because a lower amount of gamma-ray excitation energy is required. Thus, the patient is exposed to a lower dose of radioactive material. Shorter decay time is preferred because the scan time can be reduced, resulting in more efficient use of the PET system and better observation of the motion of a body organ. Higher stopping power is preferred because only a smaller quantity of scintillator material is needed. Thus, thinner detectors are possible, resulting in lower cost of manufacture. A thinner detector also has an advantage of reducing the absorption of emitted light.

The present invention provides a cerium-doped alkaline earth hafnium oxide scintillator that is efficiently excitable by gamma radiation and efficiently emits light in the range of near-ultraviolet radiation to blue visible light from about 350 nm to about 500 nm. Many photoemissive materials can be conveniently used for detecting light in this range of wavelengths; for example, compounds of alkali metals with antimony dopant. In one aspect of the present invention, the scintillator of the present invention is a polycrystalline cerium-doped alkaline earth hafnium oxide containing at least an alkaline earth metal selected from the group consisting of Ba, Sr, Ca, and combinations thereof. The scintillator has a general formula of $AHfO_3$:Ce; wherein A is at least an alkaline earth metal selected from the group consisting of Ba, Sr, Ca, and combinations thereof; the atomic ratio of A:Hf is from about 0.9:1 to about 1.1:1, preferably from about 0.95:1 to about 1.05:1; and Ce is present in an amount from about 0.005 to about 5 atom percent, preferably in the range from about 0.01 to about 2 atom percent, and more preferably from about 0.01 to about 1 atom percent.

In one aspect of the present invention, the alkaline earth metal is partially substituted with at least a trivalent ion in an amount up to about 50 atom percent of the alkaline earth metal. Non-limiting examples of trivalent ions are ions of lanthanum, gadolinium, and lutetium. Such a scintillator has a general formula of $A_{1-x-y}M^{III}_xCe_yHf_{1-(x+y)/4}O_3$; wherein $0<x \leq 0.5$; $0<y \leq 0.05$; A is at least an alkaline earth metal selected from the group consisting of Ba, Sr, Ca, and combinations thereof; and $M^{III}$ is at least a trivalent ion. In this embodiment, the charge of the trivalent ion $M^{III}$ is compensated by a combination of both the alkaline earth metal ions and the hafnium ion.

In another aspect of the present invention, the alkaline earth metal is partially substituted with at least a trivalent ion in an amount up to about 20 atom percent of the alkaline earth metal. Non-limiting examples of trivalent ions are ions of lanthanum, gadolinium, and lutetium. Such a scintillator has a general formula of $A_{1-3x-3y}M^{III}_{2x}Ce_{2y}HfO_3$; wherein $0<x \leq 0.1$; $0<y \leq 0.025$; A is at least an alkaline earth metal selected from the group consisting of Ba, Sr, Ca, and combinations thereof; and $M^{III}$ is at least a trivalent ion. In this embodiment, the charge of the trivalent ion $M^{III}$ is compensated by only the alkaline earth metal ions.

In another aspect of the present invention, hafnium is partially substituted with at least a trivalent ion in an amount up to about 5 atom percent of hafnium. Non-limiting examples of trivalent ions are ions of lutetium, ytterbium, gadolinium, holmium, aluminum, gallium, and indium. Such a scintillator has a general formula of $A_{1-y}Ce_yHf_{1-z}M^{III}_zO_3$; wherein $0<y \leq 0.05$; $0<z \leq 0.05$; A is at least an alkaline earth metal selected from the group consisting of Ba, Sr, Ca, and combinations thereof; and $M^{III}$ is at least a trivalent ion.

In another aspect of the present invention, hafnium is partially substituted with at least a tetravalent ion in an amount up to about 20 atom percent of hafnium. Non-limiting examples of tetravalent ions are ions of zirconium, tin, tellurium, titanium, germanium, and silicon. Such a scintillator has a general formula of $A_{1-y}Ce_yHf_{1-z}M^{IV}_zO_3$; wherein $0<y \leq 0.05$; $0<z \leq 0.05$; A is at least an alkaline earth metal selected from the group consisting of Ba, Sr, Ca, and combinations thereof; and $M^{IV}$ is at least a tetravalent ion. In one embodiment, $M^{IV}$ is selected from the group consisting of zirconium, tin, tellurium, titanium, germanium, silicon, and combinations thereof.

In another aspect of the present invention, ions of the at least an alkaline earth metal and hafnium are partially substituted with a combination of a trivalent ion and a divalent ion. Non-limiting examples of trivalent ions are ions of lanthanum, gadolinium, and lutetium. Non-limiting examples of divalent ions are ions of magnesium and calcium. Such a scintillator has a general formula of $A_{1-2y-2v}Ce_{2y}M^{III}_{2v}Hf_{1-y-v}M^{II}_{y+v}O_3$; wherein $0<y\leq0.025$; $0<v\leq0.1$; A is at least an alkaline earth metal selected from the group consisting of Ba, Sr, Ca, and combinations thereof; $M^{III}$ is at least a trivalent ion; and $M^{II}$ is at least a divalent ion.

In one embodiment, the alkaline earth hafnium oxide scintillator material advantageously comprises lutetium or aluminum that is present in an amount from about 0.005 to about 2 atom percent, preferably from about 0.01 to about 1 atom percent.

A scintillator composition of the present invention may be prepared by a dry or wet synthesis method. A scintillator of the present invention useful for a detection of high-energy radiation such as X, β, or γ radiation is produced by a dry synthesis method comprising the steps of: (1) providing a mixture of compounds of at least cerium, hafnium, and at least an alkaline earth metal that is selected from the group consisting of Ba, Sr, Ca, and combinations thereof; the amounts of these compounds being selected such that the final composition of the scintillator is achieved; and (2) firing the mixture at a temperature and for a time sufficient to convert the mixture to a cerium-doped alkaline earth hafnium oxide scintillator, wherein cerium is substantially in the trivalent state. In one aspect of the present invention, at least a portion of the firing is done in a reducing atmosphere, such as hydrogen, carbon monoxide, or a mixture of hydrogen and/or CO and an inert gas such as nitrogen, helium, neon, argon, krypton, xenon, or a mixture thereof.

When one or more compounds of the starting mixture is not an oxide, the mixture may be heat treated to convert non-oxides into oxides by, for example, decomposing such non-oxides. Typically, such a decomposition is substantially complete when the non-oxide is heated to a temperature in the range from about 400° C. to about 900° C.

In one embodiment, the scintillator material after the step of firing is in the form of a powder. The method can further comprise the steps of: (3) milling or pulverizing the powder to micrometer-sized particles having a size of less than about 2 micrometers, preferably less than about 0.5 micrometer, more preferably less than 0.2 micrometer; and (4) subjecting the micrometer-sized particles in a hot pressing or hot isostatic pressing to form a shaped scintillator having improved light transparency. A shaped scintillator having "improved light transparency" means that it allows at least 70 percent of light having a wavelength of about 420 nm to transmit through a thickness of about 1.5 mm. The step of hot isostatic pressing is typically conducted at a temperature in the range from about 1600° C. to about 2200° C., preferably from about 1900° C. to about 2000° C. under a pressure in the range from about 130 MPa to about 250 MPa, preferably from about 170 MPa to about 200 MPa. The shaped scintillator body may be sintered or annealed before or after the step of isostatic pressing to help to increase its density and decrease its porosity. Such a sintering or annealing is typically conducted at a temperature in the range from about 1600° C. to about 1900° C. Although the applicants do not wish to be bound by any particular theory, it is believed that the shaped polycrystalline scintillators of the present invention have improved transparency because the pore volume was drastically reduced to less than 0.05 percent, and, thus, a scintillator density near the theoretical value was obtained. It is also believed that improved transparency was also a result of the near cubic crystal structure of the scintillator achieved in the method of manufacturing of the present invention.

Compounds of at least cerium, hafnium, alkaline earth metals, and optionally other divalent, trivalent, and tetravalent ions, when desired, which compounds may be used in the preparation of the scintillators of the present invention are the inorganic compounds such as oxides, carbonates, nitrates, halides, oxyhalides, oxynitrates, and sulfates. Other suitable compounds are the oxygen-containing organic compounds. Non-limiting examples of these organic compounds are the metal salts of mono- and di-carboxylic acids containing 1 to 6 carbon atoms, esters of di-carboxylic acids containing 1 to 6 carbon atoms, metal salts of aromatic acids having 1 or 2 aromatic rings, metal acetylacetonates, metal alkoxides containing 1 to 6 carbon atoms, and metal phenoxides.

In one aspect of the present invention, cerium is provided as $CeLuO_3$ or $CeAlO_3$.

The metal compounds may be mixed together by any mechanical method including, but not limited to, stirring or blending in a high-speed blender or a ribbon blender. The metal compounds may be combined and pulverized together in a bowl mill, a hammer mill, or a jet mill. The mixing may be carried out by wet milling especially when the mixture of the metal compounds is to be made into a solution for subsequent precipitation. If the mixture is wet, it may be dried first before being fired under an oxygen-containing atmosphere at a firing temperature from about 900° C. to about 1300° C., preferably from about 1000° C. to about 1200° C. The drying may be conducted at atmospheric or subatmospheric pressure in an oxygen-containing gas; such as air, oxygen, or mixtures thereof and inert gases, such as nitrogen, helium, neon, argon, krypton, or xenon; at a temperature sufficient to remove a portion of or substantially all solvent used in the wet milling process. When the starting compounds are not oxides, it may be desirable to convert them to the corresponding oxides by heating the mixture of these compounds to a temperature above the highest decomposition temperature of these compounds. Typically, such a conversion is substantially complete at a temperature between about 400° C. and about 900° C. The firing may be conducted in a batchwise or continuous process, preferably with a stirring or mixing action to promote good gas-solid contact. The firing time depends on the quantity of the mixture to be fired, the rate of gas conducted through the firing equipment, and the quality of the gas-solid contact in the firing equipment. Typically, a firing time up to about 10 hours is adequate in an oxygen-containing atmosphere. Subsequently, the fired material can be calcined in a reducing atmosphere at a temperature and a time sufficient substantially to convert the cerium ions to its trivalent state. The calcination is typically carried out at a temperature in the range from about 1000° C. to about 1600° C., preferably from about 1000° C. to about 1500° C. and more preferably from about 1000° C. to about 1450° C. for up to 10 hours. A suitable reducing atmosphere comprises hydrogen or CO or a mixture of at least one of hydrogen and CO with an inert gas, such as nitrogen, helium, neon, argon, krypton, or xenon. The calcined material is further processed into scintillators having improved transparency as is disclosed above. For example, the calcined material may be annealed and then subject to a hot isostatic pressing as disclosed above to improve its transparency.

EXAMPLE
Making a Shaped Scintillator Article

Powder of $SrHfO_3$ containing 0.5 atomic percent cerium added as $CeLuO_3$ was produced by milling $SrCO_3$, $HfO_2$, $Ce_2(CO_3)_3$, and $Lu_2O_3$ in oxalic acid. The powder, a mixture of oxalate and oxide, was fired in air at 1200° C. for 3 hours and subsequently calcined in a reducing atmosphere that consists essentially of 10 percent (by volume) $H_2$ in nitrogen at 1400° C. for 4 hours. The powder was then milled in ethanol. After milling, the powder was dried in air and pressed at about 150–300 MPa into disks having a diameter of 12 mm and a thickness of 2 mm. The disks were sintered at 1700° C. for 4 hours in a wet hydrogen atmosphere. The sintered disks were hot isostatically pressed at 1900° C. for 2 hours at a pressure of about 207 MPa in argon. The hot isostatically pressed disks were further annealed at 1700° C. for 2 hours in wet hydrogen. The resulting disks comprise a polycrystalline scintillator composition. Light output from a finished disk under 511 keV X-ray excitation was 170 percent of a standard bismuth germanate single-crystal scintillator. The results of other similarly produced cerium-doped strontium hafnium oxide scintillators are shown in Table 1.

TABLE 1

| Cerium Content (atom percent) | Sr/Hf Ratio | Light Output (under 60 keV excitation) (BGO light output = 1) |
| --- | --- | --- |
| 0.01 | 0.95 | 2.11 |
| 1 | 0.95 | 1.50 |
| 0.01 | 1.1 | 0.05 |
| 1 | 1.1 | 0.33 |
| 1 | 1.025 | 1.34 |
| 0.505 | 1.1 | 0.34 |
| 0.01 | 1.025 | 0.17 |
| 0.505 | 0.95 | 2.03 |
| 0.505 | 1.025 | 2.35 |
| 0.369 | 1.099 | 0.59 |
| 0.961 | 1.049 | 1.13 |
| 0.189 | 1.015 | 2.59 |

The results of other similarly produced cerium-doped barium hafnium oxide scintillators are shown in Table 2.

TABLE 2

| Cerium Content (atom percent) | Ba/Hf Ratio | Light Output (under 60 keV excitation) (BGO light output = 1) |
| --- | --- | --- |
| 0.01 | 1 | 1.50 |
| 0.5 | 1 | 3.02 |
| 1 | 1 | 3.24 |

Alternatively, the scintillator compositions of the present invention may be produced in a wet method. One or more of the starting materials for the aforementioned scintillator synthesis may be compounds other than oxides that are soluble in an aqueous solution, such as nitrates, sulfates, acetates, citrates, chlorates, persilicates, oxyhalides, or organic compounds disclosed above. For example, amounts of compounds of at least cerium, hafnium, and at least an alkaline earth metal are blended and dissolved in an acid, such as nitric acid solution. Compounds of other divalent, trivalent, and/or tetravalent ions may be added into the solution, if they are desired in the final scintillator composition, as is disclosed above. The strength of the acid solution is chosen to rapidly dissolve the compounds and the choice is within the skill of a person skilled in the art. Ammonium hydroxide is then added in increments to the acidic solution containing these metals while stirring to precipitate a mixture of hydroxides containing Ce, Hf, and said at least an alkaline earth metal, and optionally other divalent, trivalent, and/or tetravalent ions as well. Other ammonium compounds, such as ammonium carbonate or ammonium oxalate, can also be used for the precipitation of compounds of Ce, Hf, and said at least an alkaline earth metal, and optionally said other ions. An alkyl ester of a di-carboxylic acid selected from the group consisting of oxalic acid, malonic acid, succinic acid, and glutaric acid may be used in place of ammonium hydroxide. An organic base; such as methanolamine, ethanolamine, propanolamine, dimethanolamine, diethanolamine, dipropanolamine, trimethanolamine, triethanolamine, or tripropanolamine; may be used in place of ammonium hydroxide. The precipitate is filtered, washed with deionized water, and dried. The dried precipitate is heated in air at between about 400° C. and about 900° C. for a sufficient time to ensure a substantially complete dehydration of the starting material and decomposition of any organic materials used. It may be desired to mill or pulverize the dried precipitate before heating. After decomposition, the mixture comprises substantially oxides of Ce, Hf, and said at least an alkaline earth metal, and optionally said other ions. The heating may be carded out at a constant temperature. Alternatively, the temperature may be ramped from ambient to and held at the final temperature for the duration of the heating. The material is then fired at a temperature in the range from about 900° C. to about 1500° C. for a sufficient time under an oxygen-containing atmosphere, such as air or a mixture of air and an inert gas. Typically, a firing time of up to about 10 hours is adequate. Subsequently, the fired material can be calcined in a reducing atmosphere at a temperature and a time sufficient substantially to convert the cerium ions to their trivalent state. The calcination is typically carried out at a temperature in the range from about 1000° C. to about 1800° C., preferably from about 1000° C. 0° C. to about 1500° C., and more preferably from about 1000° C. to about 1450° for up to 10 hours. A suitable reducing atmosphere comprises hydrogen or CO or a mixture of at least one of hydrogen and CO with an inert gas, such as nitrogen, helium, neon, argon, krypton, or xenon. The calcined material is further processed into scintillators having improved transparency as is disclosed above. The calcined materials can be further shaped into scintillator articles with or without pulverization prior to the step of shaping. The scintillator articles can be further sintered and/or annealed as disclosed above to improve their transparency.

A comparison of the properties of some of the cerium-doped alkaline earth hafnium oxide scintillators of the present invention and some of the better known commercial scintillators for PET is shown in Table 3.

TABLE 3

| | NaI:Tl | BGO | $Gd_2SiO_5:Ce^{3+}$ | $Lu_2SiO_5:Ce^{3+}$ | Present Invention |
| --- | --- | --- | --- | --- | --- |
| Density (g/cm$^3$) | 3.7 | 7.1 | 6.7 | 7.4 | 7.7–8.4 |
| Attenuation Coefficient for 511 keV Photon (cm$^{-1}$) | 0.37 | 0.95 | 0.70 | 0.89 | 0.85–0.95 |

TABLE 3-continued

|  | NaI:Tl | BGO | $Gd_2SiO_5:Ce^{3+}$ | $Lu_2SiO_5:Ce^{3+}$ | Present Invention |
| --- | --- | --- | --- | --- | --- |
| Relative Light Output | 100 | 7–12 | 30 | 30 | 20–30 |
| Primary Speed (nsec) | 230 | 300 | 40 | 40 | 35 |

In another aspect of the present invention, the composition of the scintillator and the firing temperatures are chosen such that the final scintillator is substantially a solid solution. A solid solution is most preferred because the radiation-detecting element would have a substantially uniform composition, refractive index, and higher light output.

Alternatively, a scintillator that has a composition suitable for single crystal growth may be produced in single crystal form. In this process, a seed crystal of the desired composition is introduced into a saturated solution containing appropriate compounds and new crystalline material is allowed to grow and add to the seed crystal using any well-known crystal growth method.

In another aspect of the present invention, the scintillator is incorporated in a gamma-radiation detector element of a PET system.

While various embodiments are described herein, it will be appreciated from the specification that various combinations of elements, variations, equivalents, or improvements therein may be made by those skilled in the art, and are still within the scope of the invention as defined in the appended claims.

What is claimed is:

1. A scintillator composition comprising alkaline earth hafnium oxide doped with cerium, wherein said alkaline earth metal is selected from the group consisting of barium, strontium, calcium, and combinations thereof; and an atomic ratio of said alkaline earth metal and said hafnium is from about 0.9 to about 1.1; said scintillator being capable of emitting visible light in response to high-energy radiation selected from the group consisting of X, β, and γ radiation and having improved light transparency, and wherein said scintillator composition is a polycrystalline material.

2. The scintillator composition according to claim 1, wherein said polycrystalline material has a porosity less than about 0.05 percent.

3. The scintillator composition according to claim 1, wherein said polycrystalline material has a density in a range from about 7.7 g/cm³ to about 8.4 g/cm³.

4. A scintillator composition comprising alkaline earth hafnium oxide doped with cerium, wherein said alkaline earth metal is selected from the group consisting of barium, strontium, calcium, and combinations thereof; and an atomic ratio of said alkaline earth metal and said hafnium is from about 0.9 to about 1.1; said scintillator being capable of emitting visible light in response to high-energy radiation selected from the group consisting of X, β, and γ radiation and having improved light transparency, said scintillator composition further comprising at least a trivalent ion other than cerium and having a formula of $$A_{1-x-y}M^{III}_xCe_yHf_{1-(x+y)/4}O_3$$

wherein 0<x0.5, 0<y≦0.05, A is said alkaline earth metal, and $M^{III}$ is a trivalent ion other than cerium.

5. The scintillator composition according to claim 4, wherein $M^{III}$ is selected from the group consisting of lanthanum, gadolinium, lutetium, and combinations thereof.

6. A scintillator composition comprising alkaline earth hafnium oxide doped with cerium, wherein said alkaline earth metal is selected from the group consisting of barium, strontium, calcium, and combinations thereof; and an atomic ratio of said alkaline earth metal and said hafnium is from about 0.9 to about 1.1; said scintillator being capable of emitting visible light in response to high-energy radiation selected from the group consisting of X, β, and γ radiation and having improved light transparency, said scintillator composition further comprising at least a trivalent ion other than cerium and having a formula of $$A_{1-3x-3y}M^{III}_{2x}Ce_{2y}HfO_3$$

wherein 0<x0.1, 0<y≦0.025, A is said alkaline earth metal, and $M^{III}$ is a trivalent ion other than cerium.

7. The scintillator composition according to claim 6, wherein $M^{III}$ is selected from the group consisting of lanthanum, gadolinium, lutetium, and combinations thereof.

8. A scintillator composition comprising alkaline earth hafnium oxide doped with cerium, wherein said alkaline earth metal is selected from the group consisting of barium, strontium, calcium, and combinations thereof; and an atomic ratio of said alkaline earth metal and said hafnium is from about 0.9 to about 1.1; said scintillator being capable of emitting visible light in response to high-energy radiation selected from the group consisting of X, β, and γ radiation and having improved light transparency, said scintillator composition further comprising at least a trivalent ion other than cerium and having a formula of $$A_{1-y}Ce_yHf_{1-z}M^{III}_zO_3$$

wherein 0<y≦0.05, 0<z≦0.05, A is said alkaline earth metal, and $M^{III}$ is a trivalent ion other than cerium.

9. The scintillator composition according to claim 8, wherein $M^{III}$ is selected from the group consisting of lutetium, ytterbium, gadolinium, holmium, aluminum, gallium, indium, and combinations thereof.

10. The scintillator composition according to claim 8, wherein $M^{III}$ is selected from the group consisting of lutetium, aluminum, and combinations thereof.

11. The scintillator composition according to claim 10, wherein $M^{III}$ is lutetium.

12. The scintillator composition according to claim 10, wherein $M^{III}$ is aluminum.

13. A scintillator composition comprising alkaline earth hafnium oxide doped with cerium, wherein said alkaline earth metal is selected from the group consisting of barium, strontium, calcium and combinations thereof and an atomic ratio of said alkaline earth metal and said hafnium is from about 0.9 to about 1.1; said scintillator being capable of emitting X, β and γ radiation and having improved light transparency, said scintillator composition further comprising at least one tetravalent ion and having the formula of $$A_{1-y}Ce_yHf_{1-z}M^{IV}_zO_3$$

wherein 0<y≦0.05, A is said alkaline earth metal, 0<z≦0.05 and $M^{IV}$ is a tetravalent ion selected from the group consisting of tin, tellurium, titanium, germanium, silicon and combinations thereof.

14. A scintillator composition comprising alkaline earth hafnium oxide doped with cerium, wherein said alkaline earth metal is selected from the group consisting of barium, strontium, calcium, and combinations thereof; and an atomic ratio of said alkaline earth metal and said hafnium is from about 0.9 to about 1.1; said scintillator being capable of emitting visible light in response to high-energy radiation selected from the group consisting of X, β, and γ radiation and having improved light transparency, said scintillator composition further comprising at least a trivalent ion other than cerium and a divalent ion, and having a formula of $$A_{1-2y-2v}Ce_{2y}M^{III}{}_{2v}Hf_{1-y-v}M^{II}{}_{y+v}O_3$$

wherein $0 < y \leq 0.025$, $0.1 < v \leq 0.1$, A is said alkaline earth metal, $M^{III}$ is a trivalent ion other than cerium, and $M^{II}$ is a divalent ion.

15. The scintillator composition according to claim 14, wherein $M^{III}$ is selected from the group consisting of lanthanum, gadolinium, lutetium, and combinations thereof; and $M^{II}$ is selected from the group consisting of magnesium, calcium, and combinations thereof.

16. A method for producing a cerium-doped alkaline earth hafnium oxide scintillator composition that comprises at least one alkaline earth metal selected from the group consisting of barium, strontium, calcium, and combinations thereof; said method comprising the steps of:
providing a mixture of compounds of cerium, hafnium, and said at least one alkaline earth metal;
firing said mixture in en oxygen-containing atmosphere at a firing temperature for a time sufficient to convert said mixture to a cerium-doped alkaline earth hafnium oxide;
pulverizing paid cerium-doped alkaline earth hafnium oxide to micrometer-sized particles having a size of less than about 2 micrometers;
subjecting said micrometer-sized particles to a procedure selected from the group consisting of hot pressing and hot isostatic pressing to form a shaped scintillator composition; and
annealing said shaped scintillator composition to produce said cerium-doped alkaline earth hafnium oxide scintillator composition;
wherein amounts of compounds are chosen to obtain the final desired composition of said scintillator, and said scintillator is capable of emitting visible light in response to an excitation of high-energy radiation selected from the group consisting of X, β, and γ radiation.

17. The method according to claim 16, wherein said providing further comprises providing amounts of compounds of at least an ion selected from the group consisting of divalent ions, trivalent ions other than cerium, tetravalent ions, and combinations thereof.

18. The method according to claim 16, wherein said firing in said oxygen-containing atmosphere is carried out at a temperature in a range from about 900° C. to about 1300° C. for a time of up to 10 hours.

19. The method according to claim 16, wherein said firing in said oxygen-containing atmosphere is preferably carried out at a temperature in a range from about 1000° C. to about 1200° C.

20. The method according to claim 16, wherein said annealing is conducted at a temperature in a range from about 1600° C. to about 1900° C.

21. A method for producing a shaped cerium-doped alkaline earth hafnium oxide scintillator that comprises at least one alkaline earth metal selected from the group consisting of barium, strontium, calcium, and combinations thereof, said method comprising the steps of:
providing a starting mixture of compounds of cerium, hafnium, and said at least one alkaline earth metal;
converting said compounds In said starting mixture substantially to water-insoluble oxygen-containing compounds to form a mixture of water-insoluble oxygen-containing compounds;
firing said mixture of said oxygen-containing compounds at a firing temperature for a time sufficient to convert said mixture to a cerium-doped alkaline earth hafnium oxide; and
hot isostatically pressing said cerium-doped alkaline earth hafnium oxide to form said shaped cerium-doped alkaline earth hafnium oxide scintillator;
wherein amounts of said compounds are chosen to obtain a final desired composition of said scintillator, and said scintillator is capable of emitting visible light in response to an excitation of high-energy radiation selected from the group consisting of X, β, and γ radiation.

22. The method according to claim 21 further comprising calcining said cerium-doped alkaline earth hafnium oxide under a reducing atmosphere before the step of hot isostatically pressing.

23. The method according to claim 21 further comprising annealing said shaped cerium-doped alkaline earth hafnium oxide scintillator after the step of hot isostatically pressing.

24. The method according to claim 22 further comprising annealing said cerium-doped alkaline earth hafnium oxide scintillator after the step of calcining said cerium-doped alkaline earth hafnium oxide scintillator and before the step of hot isostatic pressing.

25. The method according to claim 21, wherein said mixture further comprises compounds of at least an ion selected from the group consisting of divalent ions, trivalent ions other than cerium, tetravalent ions, and combinations thereof.

26. The method according to claim 21, wherein said compounds are selected from the group consisting of oxides, carbonates, nitrates, halides, oxyhalides, oxynitrates, sulfates, salts of mono- and di-carboxylic acids containing 1 to 6 carbon atoms, esters of di-carboxylic acids containing 1 to 6 carbon atoms, salts of aromatic acids containing up to 2 aromatic rings, acetylacetonates, alkoxides, and mixtures thereof.

27. A method for producing a cerium-doped alkaline earth hafnium oxide scintillator composition that comprises at least one alkaline earth metal selected from the group consisting of barium, strontium, calcium, and combinations thereof; said method comprising the steps of;
providing a first solution comprising compounds of at least cerium, hafnium, and said at least one alkaline earth metal;
providing a second solution selected from the group consisting of ammonium hydroxide; alkyl esters of a di-carboxylic acid selected from the group consisting of oxalic acid, malonic acid, succinic acid, and glutaric acid; amines selected from the group consisting of methanolamine, ethanolamine, propanolamine, dimethanolamine, diethanolamine, dipropanolamine, trimethanolamine, triethanolamine, and tripropanolamine; and mixtures thereof;
mixing together said first solution and said second solution to form a precipitate mixture of oxygen-containing compounds of at least cerium, hafnium, and said at least one alkaline earth metal;

separating said precipitate mixture from a supernatant liquid;

firing said precipitate mixture at a temperature and for a time sufficient to convert said dried precipitate mixture to said cerium-doped hafnium oxide scintillator composition;

wherein amounts of said compounds are chosen to obtain a final desired composition of said scintillator that is capable of emitting visible light in response to an excitation of high-energy radiation selected from the group consisting of X, $\beta$, and $\gamma$ radiation.

28. The method according to claim 27, wherein said first solution further comprises amounts of compounds of at least an ion selected from the group consisting of divalent ions, trivalent ions other than cerium, tetravalent ions, and combinations thereof.

29. The method according to claim 27 further comprising the step of calcining said cerium-doped alkaline earth hafnium oxide scintillator composition in a reducing atmosphere to produce a calcined scintillator material.

30. The method according to claim 27, wherein said firing is carried out in an oxygen-containing atmosphere at a temperature in a range from about 900° C. to about 1500° C. for a time of up to 10 hours.

31. The method according to claim 27, wherein said firing in said oxygen-containing atmosphere is preferably carried out at a temperature in a range from about 1000° C. to about 1500° C.

32. The method according to claim 29, wherein said calcining is carried out at a temperature in a range from about 1000° C. to about 1600° C. for a time of up to 10 hours.

33. The method according to claim 29, wherein said calcining is carried out at a temperature in a range from about 1000° C. to about 1500 ° C.

34. The method according to claim 27 further comprising the step of sintering said scintillator composition after firing to produce a sintered scintillator composition.

35. The method according to claim 34 further comprising the step of annealing said sintered composition after sintering.

36. A method for producing a shaped cerium-doped alkaline earth hafnium oxide scintillator that comprises at least one alkaline earth metal selected from the group consisting of barium, strontium, calcium, and combinations thereof, said method comprising the steps of:

providing a first solution that comprises amounts of compounds of at least cerium, hafnium, and said at least one alkaline earth metal;

providing a second solution selected from the group consisting of ammonium hydroxide; alkyl esters of a di-carboxylic acid selected from the group consisting of oxalic acid, malonic acid, succinic acid, and glutaric acid; amines selected from the group consisting of methanolamine, ethanolamine, propanolamine, dimethanolamine, diethanolamine, dipropanolamine, trimethanolamine, triethanolamine, and tripropanolamine; and mixtures thereof;

mixing together said first solution and said second solution to form a precipitate mixture of oxygen-containing compounds of at least cerium, hafnium, and said at least one alkaline earth metal;

separating said precipitate mixture from a supernatant liquid;

firing said precipitate mixture at a temperature and for a time sufficient to convert said precipitate mixture to a cerium-doped hafnium oxide; and hot isostatically pressing said cerium-doped hafnium oxide to form said shaped cerium-doped alkaline earth hafnium oxide scintillator;

wherein amounts of compounds are chosen to obtain a final desired composition of said scintillator that is capable of emitting visible light in response to an excitation of high-energy radiation selected from the group consisting of X, $\beta$, and $\gamma$ radiation.

37. The method according to claim 36, wherein said first solution further comprises at least a compound of at least an ion selected from the group consisting of divalent ions, trivalent ions other than cerium, tetravalent ions, and combinations thereof.

38. The method according to claim 36, wherein said firing is followed by a step of calcining said cerium-doped alkaline earth hafnium oxide in a reducing atmosphere.

39. The method according to claim 36 further comprising annealing said shaped cerium-doped alkaline earth hafnium oxide scintillator after the step of hot isostatically pressing.

40. The method according to claim 38 further comprising annealing said cerium-doped alkaline earth hafnium oxide scintillator after the step of calcining and before the step of hot isostatically pressing.

41. The method according to claim 36, wherein said firing is conducted at a firing temperature in a range from about 900° C. to about 1500° C.

42. The method according to claim 36, wherein said firing temperature is preferably in a range from about 1000° C. to about 1400° C.

43. The method according to claim 38, wherein said calcining temperature is conducted at a temperature in a range from about 1000° C. to about 1600° C.

44. The method according to claim 36, wherein said calcining temperature is preferably in a range from about 1000° C. to about 1500° C. more preferably from about 1000° C. to about 1450° C.

45. A detector element of a positron emission tomography ("PET") scanner comprising a cerium-doped alkaline earth hafnium oxide scintillator composition, wherein said alkaline earth metal is selected from the group consisting of barium, strontium, calcium, and combinations thereof; and an atomic ratio of said alkali earth metal and said hafnium is from about 0.9 to about 1.1; and said scintillator being capable of emitting visible light in response to high-energy radiation selected from the group consisting of X, $\beta$, and $\gamma$ radiation and having improved light transparency.

46. A detector element of a PET scanner comprising a cerium-doped alkaline earth hafnium oxide scintillator composition, wherein said alkaline earth metal is selected from the group consisting of barium, strontium, calcium, and combinations thereof; and an atomic ratio of said alkali earth metal and said hafnium is from about 0.95 to about 1.05; and said scintillator being capable of emitting visible light in response to high-energy radiation selected from the group consisting of X, $\beta$, and $\gamma$ radiation and having improved light transparency.

47. A detector element of a PET scanner comprising a cerium-doped alkaline earth hafnium oxide scintillator composition of claim 2.

48. A detector element of a PET scanner comprising a cerium-doped alkaline earth hafnium oxide scintillator composition of claim 3.

49. A detector element of a PET scanner comprising a cerium-doped alkaline earth hafnium oxide scintillator composition of claim 4.

50. A detector element of a PET scanner comprising a cerium-doped alkaline earth hafnium oxide scintillator composition of claim 6.

51. A detector element of a PET scanner comprising a cerium-doped alkaline earth hafnium oxide scintillator composition of claim 8.

52. A detector element of a PET scanner comprising a cerium-doped alkaline earth hafnium oxide scintillator composition of claim 13.

53. A detector element of a PET scanner comprising a cerium-doped alkaline earth hafnium oxide scintillator composition of claim 14.

54. A PET scanner comprising an X-ray detector that comprises a cerium-doped alkaline earth hafnium oxide scintillator composition, wherein said alkaline earth metal is selected from the group consisting of barium, strontium, calcium, and combinations thereof; and an atomic ratio of said alkali earth metal and said hafnium is from about 0.9 to about 1.1; and said scintillator being capable of emitting visible light in response to high-energy radiation selected from the group consisting of X, $\beta$, and $\gamma$ radiation and having improved light transparency.

55. A PET scanner comprising an X-ray detector that comprises a cerium-doped alkaline earth hafnium oxide scintillator composition, wherein said alkaline earth metal is selected from the group consisting of barium, strontium, calcium, and combinations thereof; and an atomic ratio of said alkali earth metal and said hafnium is from about 0.95 to about 1.05; and said scintillator being capable of emitting visible light in response to high-energy radiation selected from the group consisting of X, $\beta$, and $\gamma$ radiation and having improved light transparency.

56. A PET scanner comprising an X-ray detector that comprises a cerium-doped alkaline earth hafnium oxide scintillator composition of claim 2.

57. A PET scanner comprising an X-ray detector that comprises a cerium-doped alkaline earth hafnium oxide scintillator composition of claim 3.

58. A PET scanner comprising an X-ray detector that comprises a cerium-doped alkaline earth hafnium oxide scintillator composition of claim 4.

59. A PET scanner comprising an X-ray detector that comprises a cerium-doped alkaline earth hafnium oxide scintillator composition of claim 6.

60. A PET scanner comprising an X-ray detector that comprises a cerium-doped alkaline earth hafnium oxide scintillator composition of claim 8.

61. A PET scanner comprising an X-ray detector that comprises a cerium-doped alkaline earth hafnium oxide scintillator composition of claim 13.

62. A PET scanner comprising an X-ray detector that comprises a cerium-doped alkaline earth hafnium oxide scintillator composition of claim 14.

* * * * *